United States Patent [19]
Barry

[11] Patent Number: 4,571,750
[45] Date of Patent: Feb. 25, 1986

[54] ACOUSTIC MYOGRAPHY

[75] Inventor: Daniel T. Barry, Ann Arbor, Mich.

[73] Assignee: The University of Michigan, Ann Arbor, Mich.

[21] Appl. No.: 581,949

[22] Filed: Feb. 21, 1984

[51] Int. Cl.$^4$ ............................................. A61F 1/00
[52] U.S. Cl. .................................. 623/258; 128/773; 128/774; 128/782
[58] Field of Search .......................... 3/1.1; 128/473

[56] References Cited

U.S. PATENT DOCUMENTS

| | | | |
|---|---|---|---|
| 3,940,803 | 3/1976 | Weis, Jr. et al. | 3/1.1 |
| 4,226,248 | 10/1980 | Manoli | 128/773 |

FOREIGN PATENT DOCUMENTS 641957 1/1979 U.S.S.R. .............................. 128/773

OTHER PUBLICATIONS

"A Newly Created Electric Total Arm Prosthesis of Module Type Controlled by Microcomputer & Voice Command System" by Dr. H. Funakubo; Acta Medicotechnica; No. 2, 1981.

"An Ultrasonic-EMG Transducer for Biodynamic Research" by Watkin et al; Jour. Speech & Hearing Res.; vol. 21, #1, Mar. 1978.

"Low Frequency Sounds from Sustained Contraction of Human Skeletal Muscle" by Oster et al, Biophysical Journal; vol. 30, Apr. 1980.

*Primary Examiner*—Kyle L. Howell
*Assistant Examiner*—David Shay
*Attorney, Agent, or Firm*—Rohm & Monsanto

[57] ABSTRACT

Acoustic signals generated by muscles during contraction are used, in accordance with the invention, to generate signals responsive to muscle activity, measure muscle fatigue and excitation-contraction decoupling, provide a biofeedback response, control cybernetic systems, and control prosthetic devices. Such myoacoustic signals, when compared against myoelectric signals permit the extent of contraction of muscles to be compared against the excitation thereto. Moreover, a plurality of such myoacoustic signals can be compared synchronously against one another in a multichanneled recorder to analyse dynamic muscle problems, such as situations which result in poor posture and improper gait. These myoacoustic signals can also be used to drive prosthetic devices which are currently driven by myoelectric signals. It is an advantage of the present invention that myoacoustic signals can be analyzed using circuitry which is currently available and in use for analyzing myoelectric signals.

7 Claims, 13 Drawing Figures

FIG. 3-a-b-c-d-e-f

ACOUSTIC MYOGRAPHY

BACKGROUND OF THE INVENTION

This invention relates generally to systems and methods which utilize signals obtained from a living body and more particularly, to systems and methods of analyzing a human body and controlling prosthetic devices using acoustic signals obtained from skeletal muscles alone and in combination with myoelectric signals.

Considerable effort has been expended in prior years toward the extraction and analysis of electrical signals generated within living bodies. Of particular interest here are myoelectric signals which are understood to be representative of electrical excitation in skeletal muscles. It is now understood that myoelectric signals originate with the depolarization of the membranes of cells of individual muscle fibers during contraction. Such depolarization causes the generation of electrical potentials and currents which are detectable at remote locations, such as the surface of the skin. Thus, noninvasive techniques can be used to obtain the myoelectric signals, and therefore, such signals have been useful in controlling elementary prosthetic devices.

Ordinarily, myoelectric signals are obtained by placing an electrode, which may be made of a conductive, noncorrosive metal, such as silver or gold, on the surface of the skin of a living being. It is now well known that the placement of the electrode on the surface of the skin is a critical maneuver since precise placement of the electrode on the skin is required if a satisfactory signal detection is to be achieved. Generally, any slippage of the electrode from its initial location will degrade signal transmission.

In addition to the foregoing, myoelectric signal detection is adversely affected by variations in skin condition. For example, the impedance of the electrical communication between the electrode and the skin is altered substantially by the presence of perspiration. Thus, the electrical characteristics of the coupling to the skin of the electrode vary with skin condition. This is a substantial disadvantage of systems which rely upon myoelectric signals, in view of the very small amplitude of such signals.

In addition to requiring direct contact with the skin, myoelectric systems are subject to disruption by the presence of stray electrical fields. Accordingly, substantial electrical shielding is required, thereby increasing the cost and complexity of such systems.

It is a further problem with myoelectric signals that they do not contain within them complete information which characterizes muscular activity. In other words, the myoelectric signals are not representative of muscle activity, particularly after the onset of fatigue. During fatigue, excitation-contraction coupling is substantially reduced, and may in fact be near zero. Under such conditions, electrical activity of a muscle, as evidenced by the characteristics of a myoelectric signal, may appear to be normal, but little or no muscle contraction may be present. Thus, there is a need for a system which can assist in the determining of the onset of fatigue.

It has been known at least since the early nineteenth century that a rumbling-type of noise is produced when muscles are contracted. This noise-making capacity of skeletal muscles was publicized in the publication *Philosophical Transactions of the Royal Society*, pages 1-5 (1810). In this early lecture, Doctor William Hyde Wollaston describes a noise produced by contracting musculature having a frequency generally between 20 and 30 cycles per second, and amplitude which varies with the degree of force exerted by the muscle.

Much more recently, Doctors Oster and Jaffe reported in the *Biophysical Journal*, Vol 30, April 1980, pp. 119-128, in a paper entitled "Low Frequency Sounds from Sustained Contraction of Human Skeletal Muscle", that the sound produced by a muscle grows louder with the increased loading. The sound is quite loud at the commencement of the loading, but rather quickly settles to a steady volume. Such a sound is further reported as arising in the muscles themselves, and is not of vascular origin.

The acoustic signals generated by muscles, in the form of a relatively low frequency rumbling noise, can be detected by a transducer, such as a microphone, which need not be placed in direct communication with the surface of the skin. In fact, the skin can be covered by a sock. Such a covering may be particularly useful in situations where skin conditions, such as those requiring dressing or ointment, render direct communication between the microphone transducer and the skin undesirable. However, the amplitude of the acoustic signal received by the transducer decreases substantially absent direct communication between the transducer and the skin, and of course, with distance from the skin.

It is, therefore, an object of this invention to provide a system for producing signals responsive to muscle activity.

In is another object of this invention to provide a system for detecting muscle fatique.

It is a further object of this invention to provide an arrangement for monitoring signals pertaining to muscular activity in a living being without being affected by skin condition, or changes in skin condition over time, such as impedance changes which occur as a result of perspiration.

It is also an object of this invention to provide a system for producing a signal responsive to muscle activity without requiring contact with the skin.

It is yet another object of this invention to provide a system for evaluating postural problems.

It is yet a further object of this invention to provide a system for evaluating and diagnosing dynamic muscular problems, such as those which result in improper gait.

It is also another object of this invention to provide a noncontact system for facilitating biofeedback training.

It is still another object of this invention to provide a muscle activity detection system for analyzing fatigue time for the muscles of patients, particularly patients on respirators.

It is still a further object of this invention to provide a system for providing signals for controlling prosthetic devices.

It is yet still another object of this invention to provide an arrangement for detecting muscle activity utilizing a transducer which is not as location sensitive as myoelectric electrodes.

It is an additional object of this invention to provide a system for producing signals responsive to muscle activity, the system being generally unaffected by nearby electrical fields.

Additionally, it is an object of this invention to provide a muscle monitoring system which does not require substantial shielding against electrical fields.

It is a further additional object of this invention to provide a system for producing a signal coresponding to muscle activity, the system having high signal-to-noise ratio.

It is yet an additional object of this invention to provide a muscle activity monitoring and detection system which is simple, inexpensive, and which can utilize circuitry of the type used to analyse myoelectric signals.

SUMMARY OF THE INVENTION

The foregoing and other objects are achieved by this invention which provides in its various embodiments the methods and systems which utilize acoustic signals generated by muscles during contraction. The acoustic signals may be used to monitor muscular response, prognosticate the fatique characteristics of muscles and control prosthetic devices.

In accordance with a method aspect of the invention, a system is provided for determining fatigue, or excitation-contraction coupling, of a muscle or group of muscles in a living being. A first signal which is responsive to the electrical activity in a muscle or muscle group is received and compared against a second signal which is responsive to the contraction activity in the muscle or muscle group. The first signal corresponds to the electrical excitation of the muscle, while the second signal, which in a preferred embodiment corresponds to an acoustic signal generated within the living being, is responsive to muscle contraction. The comparison of the excitation characteristic and the responsive contraction of a muscle, viewed either at a point in time or over a predetermined period, enables determination of instantaneous and dynamic excitation-contraction coupling parameters.

The signal-to-noise ratio of the acoustic signal can be improved by using a differential circuit arrangement wherein acoustic signals on either side of a muscle under consideration are combined in a manner which eliminates noise common to both such signals. In one highly advantageous embodiment of the invention, the first and second signals are each subjected to the subtractive combination of differential circuitry, the respective transducers being coupled to similar, and preferrably identical, electrical circuitry. Thus, a myoelectric electrode which produces the first signal, and a microphonic transducer which produces the acoustically derived signal, may be interchangeable without requiring circuit modifications.

In accordance with a further method aspect of the invention, dynamic muscle situations, such as situations which result in poor posture or incorrect gait can be analyzed by receiving a plurality of acoustically derived signals from a living body and recording the signals. In a preferred embodiment, the signals, which correspond to muscular activity at various body locations, are recorded on a multichannel recorder which produces a visible representation of the respective waveforms on synchronized time scales.

In addition to analyzing muscle difficulties of the type noted hereinabove, an acoustic transducer may be inserted into a living body through a catheter so as to produce signals corresponding to internal muscle activity. This is useful in situations such as bladder spasms. The patient in such a situation can be catherized such that a transducer is inserted into the bladder, the fluid in the bladder performing as an acoustical transmission medium, and therefore the particular location and orientation of the transducer within the bladder is not critical. Conventional myoelectric techniques cannnot achieve any of these advantages.

Irrespective of the location of the acoustic transducer, the resulting electrical signals, which are typically analog signals, can be digitized by circuitry and supplied to a processor for analysis. The analysis of such myoacoustical signals provides significant advantages over, and different items of information from, conventional myoelectric signals.

The invention further includes within its scope an arrangement for monitoring a muscular function in a living body. Such monitoring is achieved by utilizing an acoustic transducer which converts an acoustic signal corresponding to a muscle contraction within a living being into a corresponding electrical signal. An indicator responsive to the electrical signal produces a perceptible indication responsive to a predetermined characteristic parameter of the electrical signal. In one embodiment, the predetermined characteristic parameter which is indicated corresponds to the amplitude of the electrical signal. Alternatively, the indicated parameter may correspond to a frequency component of the electrical signal. Of course, such amplitude and frequency characteristics can be combined in some embodiments of the invention.

The indicator noted herein may be arranged to be perceptible to the living being itself. Thus, the present arrangement is suitable for assisting in biofeedback training of an individual whereby control of a predetermined muscle function can be learned.

It should be noted that the present invention provides the advantage that there need not be direct communication between the transducer and the skin of the living being. This is particularly useful in situations where the skin has been damaged, such as by fire, and direct contact therewith is neither appropriate nor desirable. In addition, skin contact can be avoided where ointments or bandages have been applied to the skin. It is a highly significant advantage of the present invention that the myoacoustical signals can be detected even though a fluid is interposed between the transducer and the skin of the living being, and even if the living being is immersed in a fluid. In such a situation, it may be desirable to utilize differential circuitry for cancelling an objectionable noise propagated through the fluid. It should be noted that when contact between the transducer and the skin of the living being is to be avoided, the acoustical signals propagate more readily through a fluid, than through air. The high difference in density between the skin and the air causes the acoustical signals to be reflected back into living being at the interface of the skin and air. However, since a fluid approximates the density of skin more closely, significantly more signal energy is propagated through the skin-fluid interface.

It is a highly significant aspect of the present invention that the acoustical signals generated by contracting muscles can be utilized to control cybernetic and servo systems, such as prosthetic devices. Of course, the electrical signals produced by the acoustical transducers can be utilized to control electromechanical equipment located at a distance from the living being.

BRIEF DESCRIPTION OF THE DRAWINGS

Comprehension of the invention is facilitated by reading the following detailed description in conjunction with the annexed drawings, in which:

FIG. 7 is a waveform representation of a digitized sample of acoustic data showing resolution of a single motor unit.

DETAILED DESCRIPTION

Figure 1:
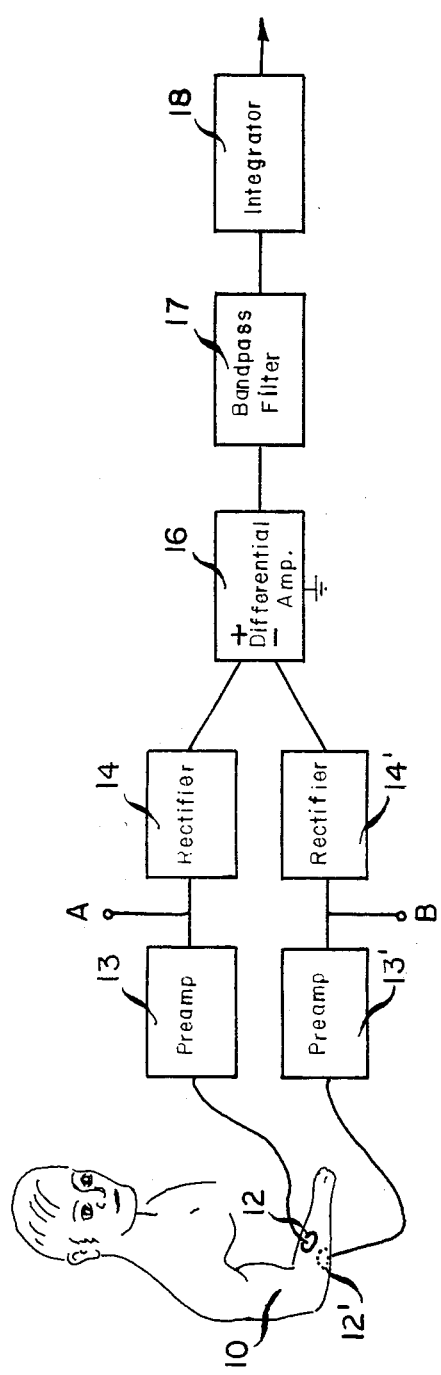
FIG. 1 is a function block diagram of a system for detecting and processing myoacoustical signals to produce a signal for driving a prosthesis.

FIG. 1 is a function block diagram of a circuit system for producing an electrical signal responsive to acoustical signals produced by contraction of muscles in a living being. As shown on this figure, a human arm 10 has coupled thereto a transducer 12, which may be a microphone, connected to a preamplifier 13. Preamplifier 13 is connected to a rectifier 14 which produces at its output a DC signal corresponding to a rectified version of the acoustic signal. Transducer 12 is arranged in the vicinity of wrist extensor muscles, while a transducer 12' is arranged in the vicinity of wrist flexor muscles.

In this particular embodiment, which is directed to driving a prosthetic or cybernetic device, a high signal-to-noise ratio is achieved by arranging transducer 12' opposite to transducer 12. Transducer 12' is connected to a respectively associated preamplifier and a rectifier, 13' and 14' respectively.

Rectifiers 14 and 14' are coupled to noninverting and inverting inputs, respectively, of a differential amplifier 16. The differential amplifier produces at its output a signal which corresponds to the difference between the outputs of rectifiers 14 and 14'. This signal is conducted to a bandpass filter which in one embodiment, may be tuned in the vicinity of 20 HZ to 30 HZ. The filtered output signal is conducted to an integrating circuit 18 which has a relatively long RC time constant, illustratively on the order of 0.2 to 1 second. The amplitude of the acoustic signals produced in arm 10 is sufficient for transducers 12 and 12' to produce an output signal of 50 millivolts.

In the specific illustrative embodiment of FIG. 1, the electric signal at the output of integrating circuit 18 is conducted to a controller 19 which may be responsive to the amplitude or the frequency thereof. The resulting drive signal is conducted to an actuator arrangement 20 which produces a mechanical force responsive to the selected one of the amplitude or frequency component of the electric signal. In this manner, a mechanical drive system responsive to myoacoustically derived information is achieved.

Figure 2:
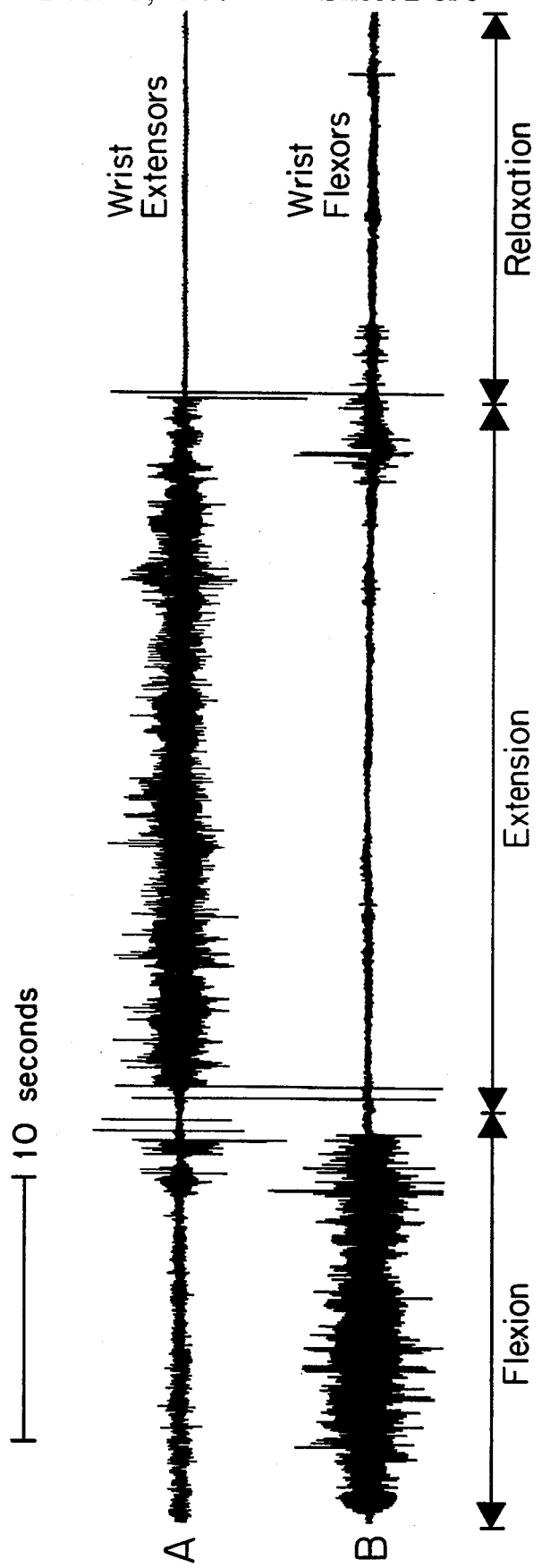
FIG. 2 illustrates waveforms of signals taken at terminals A and B of FIG. 1 during various stages of muscular activity for wrist extensors and flexors respectively.

FIG. 2 illustrates a continuous pair of waveforms taken at terminals A and B in FIG. 1. Waveforms A and B are obtained via simultaneous acoustic recording from opposite sides of the forearm of an untrained, normal subject. The figure illustrates the waveforms produced during the positions of wrist flexion, wrist extension, and then neutral wrist position. Moreover, this illustration shows that the acoustic signal has sufficient signal-to-noise ratio and dynamic range to drive a powered upper-extremity prosthesis.

FIGS. 3A to 3F show the waveforms of acoustic signals which are produced at various levels of load. FIG. 3A shows an illustrative waveform with a muscle at rest. FIG. 3B shows a slight increase in the amplitude of the waveform as a result of loading the muscle with five pounds. FIGS. 3C to 3F show the waveforms produced with respective loadings of 10 lbs., 12.5 lbs., 15 lbs. and 20 lbs. Clearly, acoustic signal intensity, or amplitude, increases as loading is applied.

Figure 4:
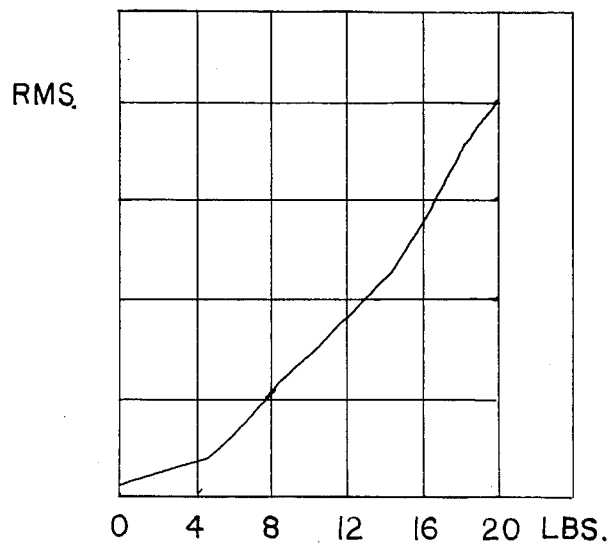
FIG. 4 is a graph illustrating the RMS amplitude of myoacoustic signals plotted against load.

The foregoing is illustrated in the graphical plot of FIG. 4 which shows the manner in which the RMS magnitude of the acoustic signal increases with the loading weight.

Figure 3:
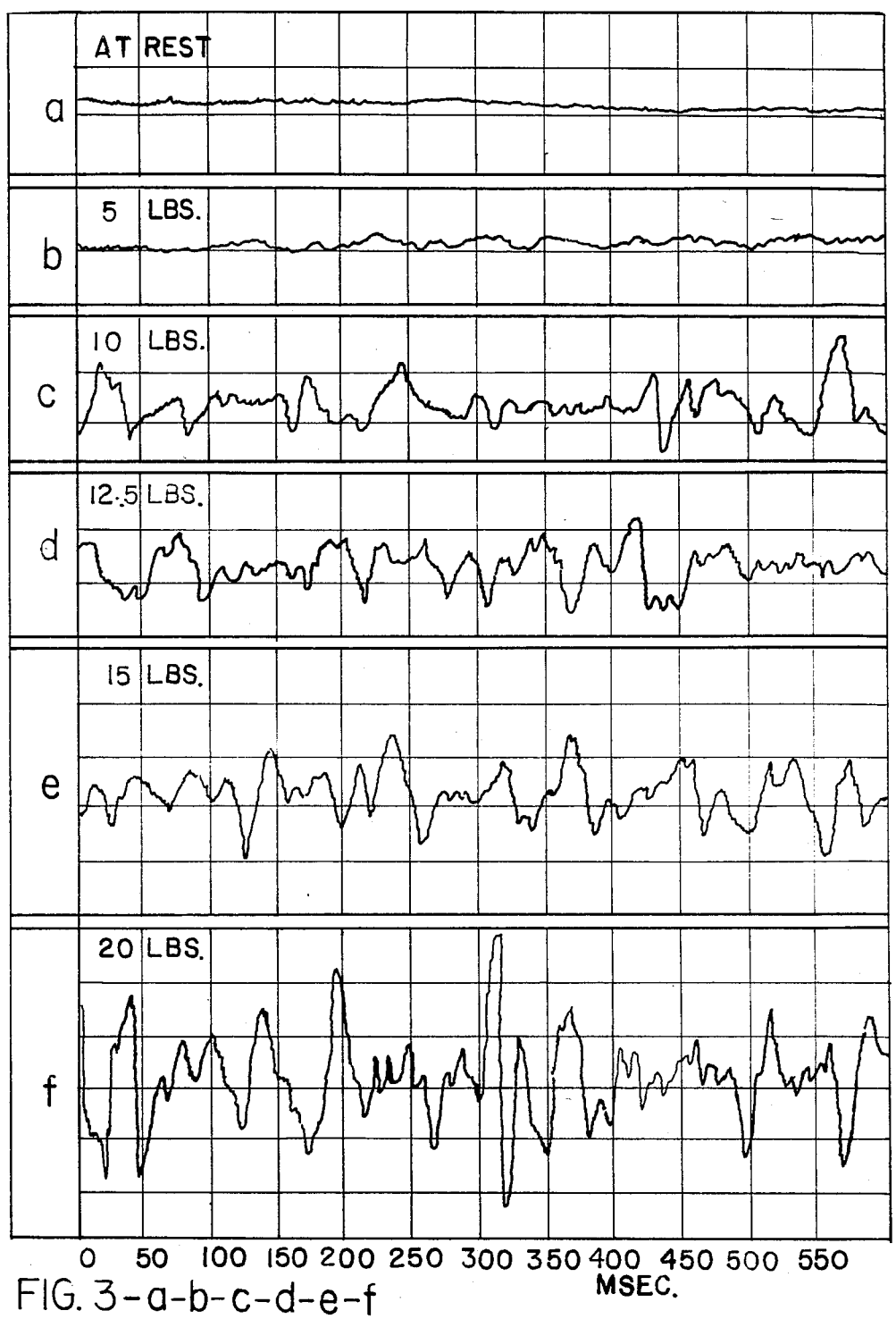
FIGS. 3A to 3F illustrate acoustical signal waveforms produced by muscles contracting against different weights.
Figure 5:
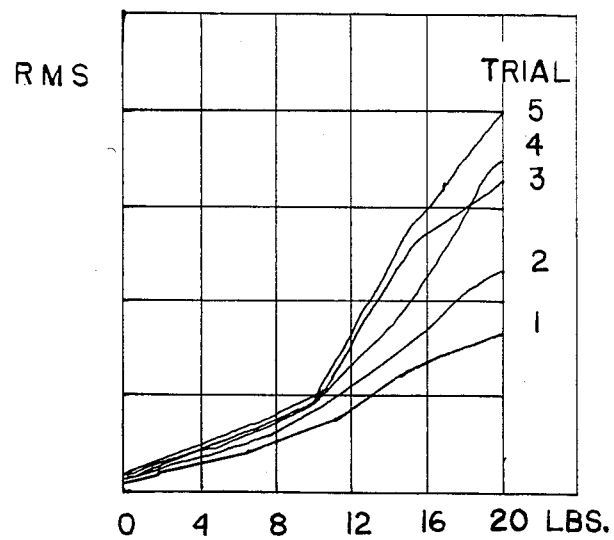
FIG. 5 is a plot illustrating increases in the amplitude of an acoustic signal in response to the onset of fatigue.

FIG. 5 is similar to the plot of FIG. 3 but shows the effects of loading over a period of time. In FIG. 5, five trials were taken, and it is evident that the RMS amplitude of the acoustic signals increases for each subsequent trial, as a result of an increasing level of fatigue.

Figure 6:
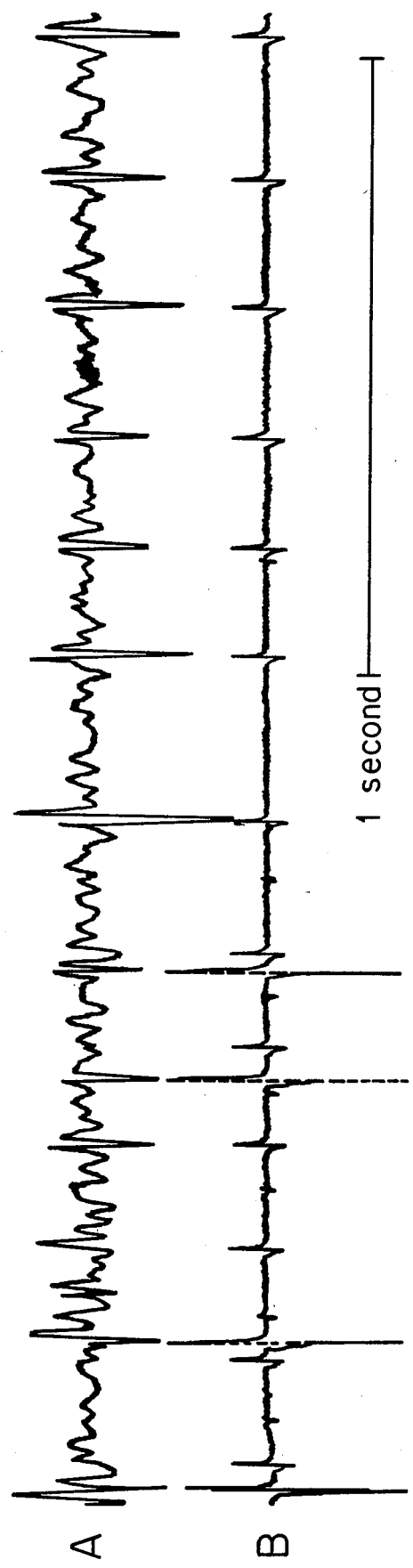
FIGS. 6A and 6B are waveforms of myoacoustic and electromyographic signals respectively, recorded simultaneously.
Figure 1:
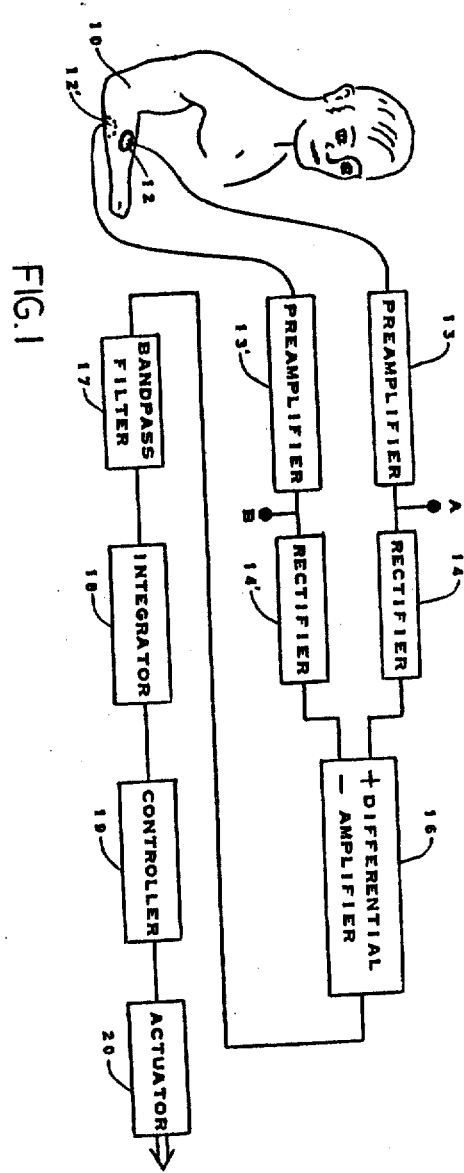

FIGS. 6A and 6B are simultaneously recorded waveforms or myoacoustic and myoelectric signals, respectively. It is sometimes possible to isolate individual motor units simultaneously using myoelectric and myoacoustic signals.

FIG. 7 shows a digitized sample of acoustic data demonstrating the resolution of a single motor unit. This is provided by flexing a muscle only very slightly.

Although the invention has been disclosed in terms of specific embodiments and applications, persons skilled in the art, in light of this teaching, can generate additional embodiments without exceeding the scope or departing from the spirit of the claimed invention. Accordingly, it is to be understood that the drawings and descriptions in this disclosure are proffered to facilitate comprehension of the invention and should not be construed to limit the scope thereof.

What is claimed is:

1. A cybernetic system comprising:
   acoustic transducer means adapted to be coupled to a living being for producing an electric signal responsive to a myoacoustic signal produced by said living being, said myoacoustic signal being responsive to contraction and relaxation states of skeletal muscles of said living being; and
   drive means for exerting a mechanical force responsive to said electric signal.

2. The cybernetic system of claim 1 wherein said drive means further comprises:
   actuator means for exerting said mechanical force; and
   signal processing means for receiving said electrical signal at an input thereof, and producing at an output thereof a drive signal responsive to a predetermined characteristic parameter of said electric signal.

3. The cybernetic system of claim 2 wherein said actuator means is a prosthetic device adapted to be coupled to the living being in place of a body member of the living being.

4. The cybernetic system of claim 1 wherein there is further provided amplitude-responsive control means for controlling said mechanical force exerted by said drive means in response to an amplitude of said electric signal.

5. The cybernetic system of claim 1 wherein there is further provided frequency-responsive control means for controlling said mechanical force exerted by said drive means in response to a frequency component of said electric signal.

6. The cybernetic system of claim 1 wherein said acoustic transducer means is adapted to communicate directly with an outer surface of the skin of said living being.

7. The cybernetic system of claim 1 wherein there is further provided acoustic signal transmission means adapted to be interposed between said living being and said acoustic transducer means.

* * * * *

UNITED STATES PATENT AND TRADEMARK OFFICE
CERTIFICATE OF CORRECTION

PATENT NO.  : 4,571,750

DATED       : February 25, 1986

INVENTOR(S) : Daniel T. Barry

It is certified that error appears in the above-identified patent and that said Letters Patent is hereby corrected as shown below:

Column 1, line 15, delete "representive" and insert therefore -- representative --.

Column 2, line 30, delete "In" and insert therefor -- It --.

Column 3, line 6, delete "analyse" and insert therefor -- analyze --.

Column 4, line 49, after "into" insert -- the --.

In the Drawing:

ABSTRACT page and sheet 1 of 5, delete the drawing (FIG. 1) and replace with the annexed substitute drawing.

Signed and Sealed this

Twenty-first Day of October, 1986

[SEAL]

Attest:

DONALD J. QUIGG

Attesting Officer        Commissioner of Patents and Trademarks

United States Patent [19]

Barry

[11] Patent Number: 4,571,750

[45] Date of Patent: Feb. 25, 1986

[54] ACOUSTIC MYOGRAPHY

[75] Inventor: Daniel T. Barry, Ann Arbor, Mich.

[73] Assignee: The University of Michigan, Ann Arbor, Mich.

[21] Appl. No.: 581,949

[22] Filed: Feb. 21, 1984

[51] Int. Cl.[4] .............................................. A61F 1/00
[52] U.S. Cl. ................................... 623/258; 128/773;
128/774; 128/782
[58] Field of Search .............................. 3/1.1; 128/473

[56] References Cited

U.S. PATENT DOCUMENTS 3,940,803  3/1976  Weis, Jr. et al. .......................... 3/1.1
4,226,248  10/1980  Manoli .............................. 128/773

FOREIGN PATENT DOCUMENTS 641957  1/1979  U.S.S.R. ............................. 128/773

OTHER PUBLICATIONS

"A Newly Created Electric Total Arm Prosthesis of Module Type Controlled by Microcomputer & Voice Command System" by Dr. H. Funakubo; Acta Medicotechnica; No. 2, 1981.
"An Ultrasonic-EMG Transducer for Biodynamic Research" by Watkin et al; Jour. Speech & Hearing Res.; vol. 21, #1, Mar. 1978.
"Low Frequency Sounds from Sustained Contraction of Human Skeletal Muscle" by Oster et al, Biophysical Journal; vol. 30, Apr. 1980.

Primary Examiner—Kyle L. Howell
Assistant Examiner—David Shay
Attorney, Agent, or Firm—Rohm & Monsanto

[57] ABSTRACT

Acoustic signals generated by muscles during contraction are used, in accordance with the invention, to generate signals responsive to muscle activity, measure muscle fatigue and excitation-contraction decoupling, provide a biofeedback response, control cybernetic systems, and control prosthetic devices. Such myoacoustic signals, when compared against myoelectric signals permit the extent of contraction of muscles to be compared against the excitation thereto. Moreover, a plurality of such myoacoustic signals can be compared synchronously against one another in a multichanneled recorder to analyse dynamic muscle problems, such as situations which result in poor posture and improper gait. These myoacoustic signals can also be used to drive prosthetic devices which are currently driven by myoelectric signals. It is an advantage of the present invention that myoacoustic signals can be analyzed using circuitry which is currently available and in use for analyzing myoelectric signals.

7 Claims, 13 Drawing Figures

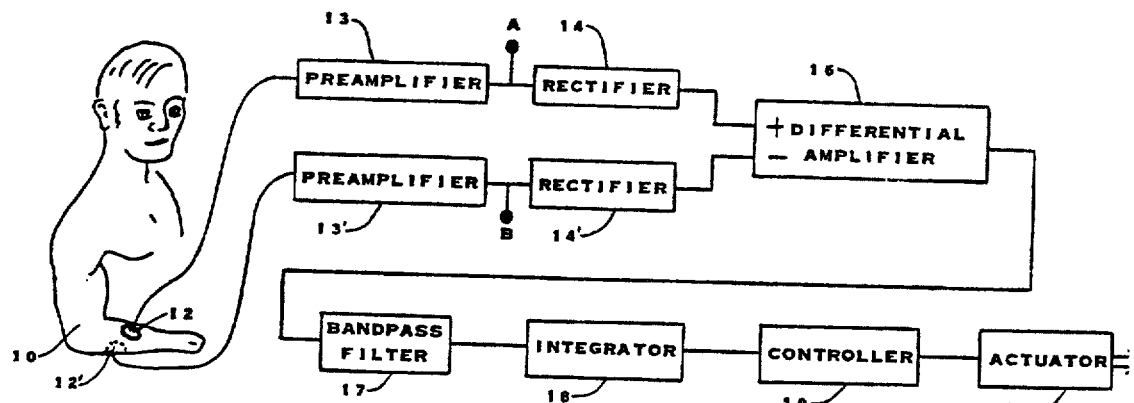

FIG.1